(12) United States Patent
Zhu et al.

(10) Patent No.: US 11,951,325 B2
(45) Date of Patent: Apr. 9, 2024

(54) PHOTON COLD GEL AND FABRICATION LINE THEREOF

(71) Applicant: SHANDONG ZHUSHI PHARMACEUTICAL GROUP CO., LTD., Heze (CN)

(72) Inventors: Kunfu Zhu, Heze (CN); Lei Zhu, Heze (CN)

(73) Assignee: SHANDONG ZHUSHI PHARMACEUTICAL GROUP CO., LTD., Heze (CN)

( * ) Notice: Subject to any disclaimer, the term of this patent is extended or adjusted under 35 U.S.C. 154(b) by 1262 days.

(21) Appl. No.: 16/550,433

(22) Filed: Aug. 26, 2019

(65) Prior Publication Data
US 2020/0289842 A1    Sep. 17, 2020

(30) Foreign Application Priority Data
Mar. 13, 2019  (CN) .......................... 201910188993.2

(51) Int. Cl.
| | |
|---|---|
| *A61N 5/06* | (2006.01) |
| *A61K 9/70* | (2006.01) |
| *A61K 36/282* | (2006.01) |
| *A61K 36/286* | (2006.01) |
| *A61K 36/48* | (2006.01) |

(Continued)

(52) U.S. Cl.
CPC ............ *A61N 5/0616* (2013.01); *A61K 9/703* (2013.01); *A61K 36/282* (2013.01); *A61K 36/286* (2013.01); *A61K 36/48* (2013.01); *A61K 36/65* (2013.01); *A61K 41/00* (2013.01); *A61M 35/00* (2013.01); *A61M 37/00* (2013.01); *B01J 19/123* (2013.01); *A61M 2037/0007* (2013.01); *A61N 5/00* (2013.01); *A61N 2005/002* (2013.01);

(Continued)

(58) Field of Classification Search
CPC .......... A61N 5/0616; A61N 5/00; A61N 5/06; A61N 2005/002; A61K 9/703; A61K 36/282; A61K 36/286; A61K 36/48; A61K 36/65; A61K 41/00; A61M 35/00; A61M 37/00; A61M 2037/0007; B01J 19/123; B30B 1/00; B30B 11/34; B65G 9/00
USPC ......................................................... 53/285
See application file for complete search history.

(56) References Cited

U.S. PATENT DOCUMENTS

| | | | | |
|---|---|---|---|---|
| 7,707,807 B2 * | 5/2010 | Py | ........................... | B65B 3/003 53/426 |
| 10,843,834 B2 * | 11/2020 | Ehrmann | ............... | B29C 66/924 |

(Continued)

*Primary Examiner* — Sameh Tawfik
(74) *Attorney, Agent, or Firm* — McClure, Qualey & Rodack, LLP

(57) ABSTRACT

A photon cold gel includes a cold gel body, wherein a non-woven fabric is arranged at the top of the cold gel body. A plurality of medicine storing cavities is formed under the cold gel body. Medicine bags are separately and fixedly arranged in each of the medicine storing cavities. Each of the medicine bags includes a ventilated cotton cloth, wherein medicines are loaded in the ventilated cotton cloth, a drainage tube which penetrates upwards through the cold gel body and is flush with the top of the non-woven fabric, is fixedly connected to the upper part of each of the medicine bags. Finally, a sealing plug is arranged at the top of each drainage tube. The present photon cold gel is able to form a micro magnetic field via the randomly distributed magnetic powder to treat human body by magnetic therapy while maintaining its primary function.

5 Claims, 1 Drawing Sheet

(51) Int. Cl.
  *A61K 36/65* (2006.01)
  *A61K 41/00* (2020.01)
  *A61M 35/00* (2006.01)
  *A61M 37/00* (2006.01)
  *B01J 19/12* (2006.01)
  *A61N 5/00* (2006.01)
  *B30B 11/00* (2006.01)
  *B30B 11/34* (2006.01)
  *B65G 9/00* (2006.01)

(52) U.S. Cl.
  CPC ............... *A61N 5/06* (2013.01); *B30B 11/00* (2013.01); *B30B 11/34* (2013.01); *B65G 9/00* (2013.01)

(56) References Cited

U.S. PATENT DOCUMENTS

| | | | | |
|---|---|---|---|---|
| 2010/0287888 | A1* | 11/2010 | Shackelford | B65B 47/04 53/559 |
| 2011/0252750 | A1* | 10/2011 | Koike | B65B 9/087 53/479 |
| 2018/0028796 | A1* | 2/2018 | Hamamoto | B32B 7/12 |
| 2018/0311486 | A1* | 11/2018 | Park | A61M 37/0015 |
| 2020/0384501 | A1* | 12/2020 | Berry | B05C 21/00 |
| 2022/0283476 | A1* | 9/2022 | Eden | H01S 5/0092 |

\* cited by examiner

PHOTON COLD GEL AND FABRICATION LINE THEREOF

TECHNICAL FIELD

The present invention relates to the field of gel manufacturing equipment, in particular to photon cold gel and fabrication line thereof.

BACKGROUND ART

The cold gel has many functions and it is often used to relieve pain and inflammation, with its strong heat conductivity, little irritation to the skin and no damage to the probe, it is an ideal heat conducting, light transmitting and skin tender special medium. The whitening effect is always improved with the high heat conduction, penetration and absorption.

The photon cold gel is a kind of gel applicable for beauty projects like photon, electric light synergy, hair removal, freckle lightening and electric wave skin lifting. And the photon cold gel usually cooperates with photon therapy equipment to achieve thermal insulation and light conduction effect. There are still some shortcomings in the current photon cold gel, such as poor medicine absorption effect during treatment which could not help patients absorb the medicine effect quickly after use. The present invention mainly aims to make some improvements on the existing photon cold gel, so as to better meet people's needs.

SUMMARY OF INVENTION

In order to solve technical problems mentioned above, the technical solutions adopted in the present invention are: the photon cold gel comprises an cold gel body, wherein a non-woven fabric is arranged at the top of the cold gel body; a plurality of medicine storing cavities are formed in the bottom of the cold gel body; medicine bags are separately and fixedly arranged in each of the medicine storing cavities; each of the medicine bags comprises a ventilated cotton cloth, wherein traditional Chinese medicines are loaded in the ventilated cotton cloth, a drainage tube which penetrates upwards through the cold gel body and is flush with the top of the non-woven fabric, is fixedly connected to the upper part of each of the medicine bags; and a sealing plug is arranged at the top of the drainage tube. To further increase the absorption rate of the medicine, it is possible to open each sealing plug and inject through the drainage tube the ionized water or liquid medicine to promote the mixing of traditional Chinese medicines inside the medicine bags, and by heating with the photon therapy equipment, the medicines could take effects quickly, and the effects of medicines on blood circulation are improved.

Preferentially, the traditional Chinese medicine comprises following ingredients in parts by weight 10-15 parts of safflower extract, 10-15 parts of caulis spatholobi extract 5-10 parts of red peony extract and 5-10 parts of diverse wormwood herb. And the traditional Chinese medicine bags are arranged at the part in contact with the human body, of the cold gel body, and the medicines could penetrate through the skin of the human body, so that through cooperation with photon treatment equipment, the medicines could be promoted to enter the human bodies, and blood circulation is promoted.

The corresponding production line for producing the photon cold gel comprises a coating machine used for producing the cold gel, wherein a conveyor belt is arranged at the downstream of the coating machine, and outside the conveyor belt is successively arranged a primary drying compartment, a pressing die compartment, a medical bag stitching and assembly compartment, a ultraviolet irradiation compartment, a secondary drying and shaping compartment and a collecting compartment along the conveying direction from the upstream to the downstream, which could ensure the manufacturing process is fast and effective, strictly sterilized by ultraviolet irradiation, and the whole production line is fast and convenient.

Preferentially, the primary drying compartment is provided with a plurality of primary dryer fans at the top of the internal compartment, the opening at the bottom of primary dryer fan is set slanting toward the side of the coating machine. With the flowing direction of hot drying air opposite to the direction of the cold gel process a better drying effect can be achieved.

Preferentially, the pressing die compartment is fixedly provided with a plurality of pressing die electric cylinders at the top of the internal compartment, the lower end of the piston rod at the bottom of pressing die electric cylinder is fixedly connected to a pressing die tool, the pressing die tool comprises a pressing die block used for pressing out the medicine storing cavity and the bottom center of the pressing die block is fixedly connected to a pressing die cutter for pressing out the installation cavity where the drainage tube is placed.

Preferentially, the medicine bag stitching and assembly compartment is used for the operator to quickly install the connected medicine bags, the drainage tubes and the sealing plugs into the corresponding medicine storing cavities and installation cavities so as to facilitate subsequent shaping and fixing.

Preferentially, inside the ultraviolet irradiation compartment is provided a plurality of ultraviolet lamps and throughout the manufacturing process, apply the ultraviolet radiation for strict sterilization.

Preferentially, the secondary drying compartment is provided with a plurality of secondary dryer fans at the top of its internal compartment, the openings at the bottom of secondary dryer fans are set slanting toward the side of the coating machine, and the flowing direction of hot drying air is opposite to the direction of the cold gel process to achieve a better drying effect.

The beneficial effects of present invention are embodied as follows: the present photon cold gel could form a miniature magnetic field with magnetic powder which is distributed randomly therein, so that the purpose of performing miniature magnet therapy on human bodies is achieved while maintaining its original functions. And the traditional Chinese medicine bag is arranged at the part in contact with the human body, of the cold gel body, and the medicines could penetrate through the skin of the human body, so that through cooperation of the traditional Chinese medicines and photon treatment equipment, the medicines could be promoted to enter the human bodies, and blood circulation is promoted; meanwhile, to further increase the absorption rate of the medicine, each sealing plug could be opened and through the drainage tube the ionized water or liquid medicine could be injected to promote the mixing of traditional Chinese medicines inside the medicine bags, then heated with the help of the photon therapy equipment, medicines could take effects quickly and the effects of medicines on blood circulation are improved; moreover, fabrication of the photon cold gel via the fabrication line is fast and quick, and ultraviolet irradiation is applied for sterilization and the process is convenient.

DESCRIPTION OF DRAWINGS

In order to explain more clearly the specific embodiments in the present invention or the technical solutions to the problems appeared in the prior art, the drawings needed in the description of the specific embodiments or prior art are briefly introduced below. In all drawings, similar elements or parts are generally identified by similar markups. In the drawings, the elements or components are not drawn to the actual scale.

The FIG. 1 is a schematic diagram showing the internal structure of the photon cold gel in the present invention.

Figure 2:
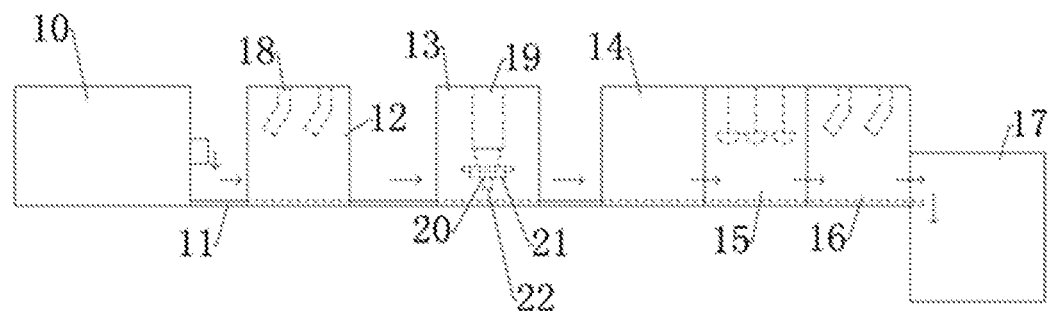

The FIG. 2 is a schematic diagram showing the corresponding production line for producing the photon cold gel in the present invention.

The markup in the present invention are indicated as follows: 1—cold gel body; 2—non-woven fabric; 3—medicine storing cavity 4—medicine bag; 5—ventilated cotton cloth; 6—traditional Chinese medicines; 7—drainage tube; 8—sealing plug; 9—magnetic powder; 10—coating machine; 11—conveyor belt 12—primary drying compartment; 13—pressing die compartment 14—medical bag stitching and assembly compartment; 15—ultraviolet irradiation compartment; 16—secondary drying and shaping compartment; 17—collecting compartment 18—primary dryer fan; 19—pressing die electric cylinder; 20—pressing die tool; 21—pressing die block; 22—pressing die cutter.

SPECIFIC EMBODIMENTS

The embodiments of the technical solutions in the present invention will be described specifically in combination with the attached drawings below. And the following embodiments are only to more clearly describe the technical solutions of the present invention and are therefore used only as examples, and could not be used to limit the scope of protection of present invention.

Figure 1:
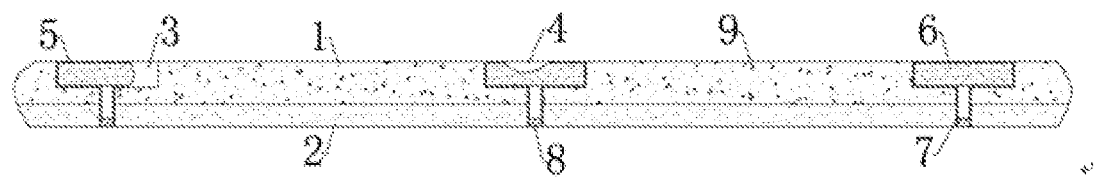

As shown in FIG. 1-2, the photon cold gel comprises an cold gel body(1), wherein a non-woven fabric(2) is arranged at the top of the cold gel body(1); a plurality of medicine storing cavities(3) are formed in the bottom of the cold gel body(1); medicine bags(4) are separately and fixedly arranged in each of the medicine storing cavities(3); each of the medicine bags(4) comprises a ventilated cotton cloth(5), wherein traditional Chinese medicines(6) are loaded in the ventilated cotton cloth(5), a drainage tube(7) which penetrates upwards through the cold gel body(1) and is flush with the top of the non-woven fabric(2), is fixedly connected to the upper part of each of the medicine bags(4); and a sealing plug(8) is arranged at the top of the drainage tube(7). To further increase the absorption rate of the medicine, each sealing plug (8) could be opened and through the drainage tube the ionized water or liquid medicine could be injected to promote the mixing of traditional Chinese medicines (6) inside the medicine bags (4), then by heating with the photon therapy equipment, medicines could take effects quickly and the effects of medicines on blood circulation are improved.

Preferentially, the granular magnetic powder (9) is distributed randomly inside the photon cold gel body (1). The present cold gel is provided with magnetic powder on the basis of cold gel (9), so that the present photon cold gel could form a miniature magnetic field with magnetic powder (9) which is distributed randomly therein, thereby achieving the purpose of performing miniature magnet therapy on human bodies while maintaining its original functions.

Preferentially, the traditional Chinese medicine (6) comprises following ingredients in parts by weight 10-15 parts of safflower extract, 10-15 parts of caulis spatholobi extract, 5-10 parts of red peony extract, and 5-10 parts of diverse wormwood herb. The traditional Chinese medicine bag (4) is arranged at the part in contact with the human body, of the cold gel body (1), and the medicines could penetrate through the skin of the human body, so that through cooperation of the traditional Chinese medicines and photon treatment equipment, the medicines could be promoted to enter the human bodies, and blood circulation is promoted. The corresponding production line for producing the photon cold gel comprises a coating machine (10) used for producing the cold gel, a conveyor belt (11) is arranged at the downstream of the coating machine (10), and outside the conveyor belt(11) is successively arranged a primary drying compartment (12), a pressing die compartment (13), a medical bag stitching and assembly compartment (14), a ultraviolet irradiation compartment (15), a secondary drying and shaping compartment (16) and a collecting compartment (17) along the conveying direction and from the upstream to the downstream, which could ensure the manufacturing process is fast and effective, strictly sterilized by ultraviolet irradiation, and the whole production line is fast and convenient.

Preferentially, the primary drying compartment is provided with a plurality of primary dryer fans at the top of its internal compartment, the opening at the bottom of each primary dryer fan is set slanting toward the side of the coating machine, and that the flowing direction of hot drying air is opposite to the direction of the cold gel process could achieve a better drying effect.

Preferentially, the pressing die compartment (13) is fixedly provided with a plurality of pressing die electric cylinders (19) at the top of the internal compartment, the lower end of the piston rod at the bottom of pressing die electric cylinder (19) is fixedly connected to a pressing die tool (20), the pressing die tool (20) comprises a pressing die block (21) used for pressing out the medicine storing cavity (3) and the bottom center of the pressing die block (21) is fixedly connected to a pressing die cutter (22) used for pressing out the installation cavity where the drainage tube (7) is placed.

Preferentially, the medicine bag stitching and assembly compartment (14) is used for the operator to quickly install the connected medicine bags (4), the drainage tubes (7) and the sealing plugs (8) into corresponding medicine storing cavities(3) and installation cavities so as to facilitate subsequent shaping and fixing.

Preferentially, inside the ultraviolet irradiation compartment (15) is provided a plurality of ultraviolet lamps and during the manufacturing process, the ultraviolet radiation is applied for strict sterilization.

Preferentially, the secondary drying compartment (16) is provided with a plurality of secondary dryer fans at the top of its internal compartment, the opening at the bottom of each secondary dryer fan is set slanting toward the side of the coating machine (10), and that the flowing direction of hot drying air is opposite to the direction of the cold gel fabrication process could achieve a better drying effect.

The cold gel body produced by the coating machine(10) is combined with the non-woven fabric and conveyed by the conveyor belt(11) to successively pass through the primary drying compartment(12), pressing die compartment(13), medical bag stitching and assembly compartment(14), ultraviolet irradiation compartment(15), primary drying and shaping compartment(16) and collecting compartment(17), the cold gel is dried firstly in the primary drying compartment(12), then the primarily dried cold gel passes through the pressing die compartment(13) to be pressed by the pressing die cutter (20) iteratively driven by the pressing die electric cylinder(19), and before starting the device, it is necessary to have the equipment debugging personnel to adjust the working speed of the coating machine(10) and the conveying speed of the conveyor belt (11) to be consistent to the pressing speed of the pressing die cylinder (19), and the adjustment of these parameters is familiar to technical personnel in the field and does not belong to the improvement of this application which is therefore unnecessary to elaborate on them, after then it passes through the medical bag stitching and assembly compartment (14) for manually placing medicine bags, and other ways for placing the medicine bags could be applied when the output is large. The production line in the present invention is mainly used where output is small, and the assembled cold gel is sterilized by ultraviolet irradiation and dried again, then enters into the collecting compartment for collection and waits for subsequent processing procedure.

The above embodiments are used only to illustrate the technical solutions in present invention but not to restrict it; Notwithstanding the detailed description of the invention in the light of the foregoing embodiments, the ordinary technical personnel in present field shall understand that it is still possible to modify the technical solutions recorded in the foregoing embodiments, or to equivalent replace some or all of the technical features thereof; Such modification or replacement does not remove the essence of the corresponding technical solution from the scope of the technical scheme of each embodiment of the present invention, which shall be covered within the scope of the claims and specification of the invention, and any alternative improvements or changes to the embodiments of the invention shall fall within the protection of the invention for a technician in the field of technology.

All the things not specified in the invention are the public knowledge technologies of technicians in the technical field.

The invention claimed is:

1. A fabrication line for producing the photon cold gel, comprising a coating machine, wherein a conveyor belt is arranged at a downstream of the coating machine, and outside the conveyor belt is successively arranged a primary drying compartment, a die casting compartment, a medical bag stitching and assembly compartment, an ultraviolet irradiation compartment, a secondary drying and shaping compartment and a collecting compartment along a conveying direction from an upstream to the downstream, wherein the primary drying compartment is provided with a plurality of primary dryer fans at a top portion in the primary drying compartment and openings at a bottom portion of primary dryer fans are directed toward a side of the coating machine.

2. The fabrication in for the photon cold gel in accordance to claim 1, wherein the die casting compartment is fixedly provided with a plurality of die casting electric cylinders at a top portion of the die casting compartment, a lower end of a piston rod at a bottom portion of each of the plurality of pressing die electric cylinders is fixedly connected to a die casting tool, the die casting tool comprises a die casting block used for pressing out medicine storing cavities and a bottom center of the die casting block is fixedly connected to a die casting cutter used for pressing out an installation cavity for placing a drainage tube.

3. The fabrication line for the photon cold gel in accordance to claim 2, wherein the medical bag stitching and assembly compartment is used for an operator to quickly install connected medicine bags, the drainage tubes and sealing plugs into corresponding the medicine storing cavities and the installation cavities so as to facilitate subsequent shaping and fixing.

4. The fabrication line for the photon cold gel in accordance to claim 3, wherein inside the ultraviolet irradiation compartment is provided a plurality of ultraviolet lamps.

5. The fabrication line for the photon cold gel in accordance to claim 4, wherein the secondary drying compartment is provided with a plurality of secondary, dryer fans, and openings at bottom portions of secondary dryer fans are set slanting toward the side of the coating machine.

* * * * *